United States Patent
Tsukada et al.

(10) Patent No.: US 6,506,951 B1
(45) Date of Patent: Jan. 14, 2003

(54) PROCESS FOR PRODUCING BROMINATED TRIFLUOROMETHYLBENZENES

(75) Inventors: Eri Tsukada, Saitama (JP); Mikio Ujiie, Saitama (JP); Shozo Kaneda, Saitama (JP); Satoru Narizuka, Saitama (JP); Takashi Kume, Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/551,912

(22) Filed: Apr. 19, 2000

(30) Foreign Application Priority Data

Apr. 20, 1999 (JP) ............................................. 11-112550
Apr. 26, 1999 (JP) ............................................. 11-118322

(51) Int. Cl.$^7$ ............................................. C07C 22/00
(52) U.S. Cl. .................................................... 570/144
(58) Field of Search ................................. 570/206, 144

(56) References Cited

U.S. PATENT DOCUMENTS 5,792,892 A * 8/1998 Hagemann .................. 570/206

FOREIGN PATENT DOCUMENTS

| JP | 50-76029 | 6/1975 |
| JP | 9-169673 | 6/1997 |

OTHER PUBLICATIONS

McBee et al., "The Preparation of Certain Ethers of Trifluoromethyl–substituted Phenols", *J. Am. Chem. Soc.*, vol. 69, pp. 947–950 (1947).
Zh. Org. Khim. vol. 27, No. 1, pp. 125–129 (1991).
Zh. Prikl. Khim. vol. 46, No. 9, pp. 2012–2016 (1973).
McBee et al., "Bromination of Trifluoromethylbenzenes", *J. Am. Chem. Soc.*, vol. 72, pp. 1651–1653 (1950).
Murray et al., "Production of Bis(Trifluoromethyl)Benzene", *Ind. Eng. Chem.*, vol. 39, pp. 302–305 (1947).
McBee et al., "Chlorination of bis– and Chloro–bis–(perfluoroalkyl)–benzenes", *J. Am. Chem. Soc.* vol. 71, pp. 1490–1491 (1949).

* cited by examiner

*Primary Examiner*—Alan Siegel
(74) *Attorney, Agent, or Firm*—Crowell & Moring LLP

(57) ABSTRACT

The invention relates to a process for producing a brominated trifluoromethylbenzene represented by the general formula (1). This process includes brominating in a liquid or gas phase a trifluoromethylbenzene, represented by the general formula (2), by bromine in the presence of a catalyst under a condition that the bromine is coexistent with chlorine,

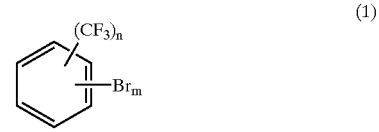
(1)

where n is an integer of 1–2, and m is an integer of 1–3

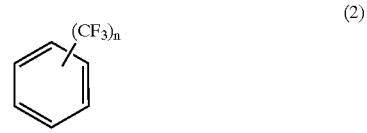

(2)

where n is an integer of 1–2. The catalyst is preferably iron chloride in the case of the bromination in a liquid phase. It is preferably activated carbon carrying thereon iron chloride in the case of the bromination in a gas phase. The trifluoromethylbenzene is turned to the brominated trifluoromethylbenzene with high reactivity and high yield.

21 Claims, No Drawings

PROCESS FOR PRODUCING BROMINATED TRIFLUOROMETHYLBENZENES

BACKGROUND OF THE INVENTION

The present invention relates to a method for producing brominated trifluoromethylbenzenes, which can be used as intermediates for medicines and agricultural chemicals.

It is known that an aromatic compound having a bromine atom(s) on its aromatic ring can be obtained by brominating its corresponding aromatic compound. Japanese Patent Unexamined Publication 50-76029 and J. Am. Chem. Soc. Vol. 69, page 947 (1947) disclose a process for producing 3-bromotrifluoromethylbenzene by brominating a trifluoromethylbenzene by bromine in the presence of iron powder or iron chloride. Zh. Org. Ehim. Vol. 27, No. 1, page 125 discloses a process for producing 3bromo-trifluoromethylbenzene by brominating a trifluoromethylbenzene using sulfur tetrafluoride, hydrogen fluoride and bromine. Zh. Prikl. Khim. Vol. 46, No. 9 (1973)page 2012 discloses a process in which 1,3-bis(trifluoromethyl) benzene is simultaneously reacted with chlorine and bromine in the presence of antimony pentachloride, thereby obtaining 3,5-bis(trifluoromethyl)bromobenzene (selectivity: 74.1%) and 3,5-bis(trifluoromethyl) chlorobenzene (selectivity: 24.6%). J. Am. Chem. Soc. Vol, 72 page 1651 (1950) discloses a process in which 1,3-bis (trifluoromethyl)benzene is simultaneously reacted with chlorine and bromine in the presence of a catalytic amount of antimony pentachloride, thereby obtaining 3,5-bis (trifluoromethyl)bromobenzene (conversion: 70%, selectivity: 74.1%). Japanese Patent Unexamined Publication 9-169673 discloses a process in which 1,3-bis (trifluoromethyl)benzene is brominated by N-bromoimide in the presence of a strong acid, thereby obtaining 3,5-bis (trifluoromethyl)bromobenzene.

Bromine is strong in metal corrosiveness. Therefore, bromination is usually conducted in a glass reactor. However, if it is tried to brominate an aromatic compound having a trifluoromethyl group(s), the bromination does not easily occur due to the electron attractive property of the trifluoromethyl group(s). Therefore, it is necessary to make the reaction condition relatively severe to get the bromination. With this, the trifluoromethyl group may be decomposed by Lewis acid catalyst used in the bromination, thereby generating hydrogen fluoride in the reaction system. This hydrogen fluoride tends to corrode glass. Therefore, it has been necessary to avoid using glass as a reactor for conducing the bromination of the above aromatic compound or to conduct such bromination with an extra care using a glass reactor.

Of conventional Lewis acid catalysts, antimony pentachloride is high in reactivity and satisfactory in selectivity. It is, however, high in corrosiveness against metal. Furthermore, antimony compounds are highly soluble in organic matters, resulting in difficulty in separating those from the product. Even if they are separated by washing, it becomes troublesome to treat waste water after the washing.

SUMMARY OF THE INVENTION

It is an object of the present invention to provide a process for producing a brominated trifluoromethylbenzene from a trifluoromethylbenzene with high conversion and high selectivity.

According to a first aspect of the present invention, there is provided a first process for producing a brominated trifluoromethylbenzene represented by the general formula (1). The first process comprises brominating in a liquid phase a trifluoromethylbenzene, represented by the general formula (2), by bromine in the presence of an iron containing catalyst under a condition that the bromine is coexistent with chlorine,

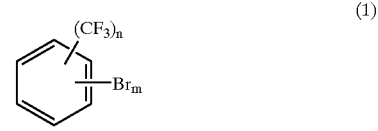

where n is an integer of 1–2, and m is an integer of 1–3

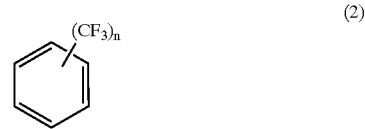

Where n is an integer of 1–2.

According to a second aspect of the present invention, there is provided a second process for producing a brominated trifluoromethylbenzene represented by the general formula (1). The second process comprises brominating in a gas phase a trifluoromethylbenzene, represented by the general formula (2), by bromine in the presence of a catalyst under a condition that the bromine is coexistent with chlorine.

DESCRIPTION OF THE REF:ERRED EMBODIMENTS

It is possible to produce a brominated trifluoromethylbenzene represented by the general formula (1) from a trifluoromethylbenzene represented by the general formula (2) with high conversion and high selectivity by both of the first and second processes.

According to the fist process, both selectivity and conversion become high by using an iron-containing catalyst such as an iron halide, particularly iron chloride, since this catalyst has a high activity in the bromination. Furthermore, the catalyst is less soluble in the product. Therefore, the catalyst can easily be separated from the product by a simple operation such as decantation, thereby simplifying the process. The separated catalyst can be used repeatedly in the bromination. Still furthermore, the iron-containing catalyst has a low corrosiveness against metal. With this, the first process can be conducted in a metal reaction vessel. Thus, the first process is a desirable process for producing the brominated trifluoromethylbenzene in an industrial scale.

According to the second process, the bromination is conducted in a gas phase, thereby simplifying the process. Furthermore, the bromination of the second process can proceed efficiently by using a catalyst containing a metal chloride (e.g., iron chloride) carried on a carrier. This catalyst has a high activity and a long lifetime in the bromination. Therefore, it is possible to produce the brominated trifluoromethylbenzene from the trifluoromethylbenzene with high conversion and high selectivity. Thus, the second process has a superior operationability and a high productivity. Furthermore, it is possible to substantially prevent corrosion of a metal reaction vessel, because bromine and chlorine are treated in a vapor phase. Thus, the second process is also a desirable process for producing the brominated trifluoromethylbenzene in an industrial scale.

In the first and second processes, the trifluoromethylbenzene represented by the general formula (1) may be trifluoromethylbenzene, 1,4-bis(trifluoromethly)benzene, 1,3-bis(trifluoromethyl)benzene, or 1,2-bis(trifluoromethyl) benzene, and may be one prepared by any process. For example, Ind. Eng. Chem. 39 [19473] 302 discloses a method for producing 1,3-bis(trifluoromethyl)benzene. This method includes the steps of (a) chlorinating methaxylene to 1,3-bis(trifluoromethyl)benzene and (b) fluorinating the 1,3-bis(trifluoromethyl)benzene by hydrogen fluoride in the absence of catalyst at a temperature of 150–20° C. J. Am. Chem. Soc. 71 [1949] 1490 discloses the same method except that the step (b) is conducted in the presence of antimony pentachloride catalyst at room temperature.

In the first and second processes, the amount of bromine used may vary depending on the amount of the brominated trifluoromethylbenzene to be produced, and is 0.5 m (m is an integer of 1–3 in the general formula (1)) moles or more for each m number. In order to produce a monobromtrifluoromethylbenzene, the amount of bromine can be 0.5 moles or more, preferably 0.5–2 moles, more preferably 0.5–1 mole, still more preferably 0.5–0.75 moles, per mole of the trifluoromethylbenzene. Alternatively, the amount of bromine can be 0.5 moles or less per mole of the trifluoromethylbenzene in order to suppress the production of polybrominated compounds generated in the course of the complete bromination of the trifluoromethylbenzene.

In the first process, chlorine is used in an amount of 1 mole or more per mole of bromine. In fact, it suffices to use 1 to about 2 moles of chlorine per mole of bromine. Furthermore, it can be adjusted to 1 to about 1.2 moles by suitably controlling the reaction. If the amount of chlorine is less than 1 mole, conversion of bromine may become too low. If chlorine is used too much, it may cause the production of chlorinated trifluoromethylbenzenes and may lower the yield of the brominated trifluoromethylbenzene. Furthermore, it makes difficult to treat chlorine during the reaction.

In the first process, although the total amount of chlorine can be put into a reactor at one time, it is preferable to add chlorine to the reactor continuously or intermittently. In fact, it is preferable that bromine in the reaction system is always in excess of chlorine in order to suppress the formation of chlorinated compounds as by-products. Therefore, it is preferable to add chlorine gradually as the reaction proceeds. In case that the reaction pressure is maintained constant by purging hydrogen chloride formed in the reaction, it is possible to reduce the loss of the unreacted chlorine and bromine chloride by returning them to the reactor using a reflux condenser connected to the exit of the reactor. When chlorine is added, it is optional to use a suitable apparatus for accelerating the gas-solid contact, such as stirrer, bubbling pipe, sparger, or the like.

In the first process, the iron-containing catalyst may be an iron halide. The catalyst may be in the form of metallic iron or an iron-containing alloy or compound when a reactor is charged with the catalyst, as long as the catalyst is in the form of halide during the reaction. In fact, the catalyst is preferably ferric chloride, ferric bromide or the like, which is easily available. Iron contained in the catalyst is in an amount of preferably 0.1–100 moles, more preferably 1–50 moles, still more preferably 5–30 moles, per 100 moles of the trifluoromethylbenzene. If it is less than 0.1 moles, the reaction rate may become too low. Even if it is greater than 100 moles, the reaction proceeds with no problem. With this, however, the reaction rate and the yield do not improve further, and the operation becomes cumbersome.

In the first process, an inert solvent may be used. Such solvent is not particularly limited and may be one of chlorine-containing solvents such as dichloromethane, chloroform, carbon tetrachloride, 1,2-dichloroethane, tetrachloroethane, pentachloroethane, trichloroethylene, and tetrachloroethylene.

In the first process, the reaction temperature may vary depending on the types of the raw material and the product. In fact, it may be in a range of about 50–200° C., preferably 90–150° C., more preferably 100–130° C. If it is lower than 50° C., the reaction may become too slow. If it is higher than 200° C., the selectivity may become too low. In particular, the reaction temperature is preferably 150° C. or lower in order to obtain monobromotrifluoromethylbenzene. The pressure of the reactor may be in a range of 1–100 kg/cm$^2$ (0.1–10 MPa), preferably 6–50 kg/cm$^2$ (0.6–5 MPa). The reactor may be made of metal such as stainless steel, Hastelloy, or Monel metal.

When a monobromotrifluoromethylbenzene is produced by intermittently adding chlorine, the first process may be conducted as follows. At first, the reactor is charged with predetermined amounts of the trifluoromethylbenzene, bromine and an iron halide and an arbitrary amount of chlorine (for example, one tenth of the total amount of chlorine necessary to complete the reaction). Then, the temperature of the reaction liquid is increased to a predetermined temperature with stirring. As the reaction proceeds, the remainder of chlorine is bubbled into the reaction liquid a little at a time. The reaction pressure is maintained constant by suitably purging hydrogen chloride formed in the reaction. The reaction is continued in this manner until the composition of the product becomes a desired one. After the reaction, the stirring is stopped to allow the reaction liquid to stand still, thereby precipitating the iron halide. After that, the supernatant liquid is taken out, thereby leaving a most part of the iron halide in the reactor. Such iron halide left in the reactor can be repeatedly used as the catalyst.

In the first and second processes, the brominated trifluoromethylbenzene represented by the general formula (1) is a brominated compound prepared by replacing "m" (i.e., an integer of 1–3 as defined in the general formula (1)) of the hydrogen atom(s) on the benzene ring of the trifluoromethylbenzene with the corresponding number of bromine atoms, with no change of the trifluoromethyl group(s). In fact, the preferential position of the hydrogen atom to be replaced with bromine atom depends on the type of the trifluoromethylbenzene. For example, it is possible to obtain as a main product of the bromination 3-bromo-trifluoromethylbenzene from trifluoromethylbenzene, 3,5-bis(trifluoromethyl)bromobenzene from 1,3-bis(trifluoromethyl)benzene, 2,5-bis(trifluoromethyl)bromobenzene from 1,4-bis(trifluoromethyl)benzene, or 3,4-bis(trifluoromethyl)bromobenzene from 1,2-bis(trifluoromethyl)benzene.

In the first process, the reaction product taken out of the reactor can be purified by one of various methods. The reaction liquid may contain bromine, chlorine and an iron halide besides organic matters containing the target product. This iron halide can be removed as an insoluble faction by decantation or filtration. The other unnecessary components can easily be removed by washing with a sodium sulfite aqueous solution and then a sodium hydroxide aqueous solution or by fash distillation, thereby obtaining a crude product of the brominated trifluoromethylbenzene, which is free of bromine, chlorine and the iron halide. This crude product can be purified by distillation to obtain the brominated trifluoromethylbenzene with high purity. This brominated trifluoromethylbenzene can be used as a raw material of various reactions. For example, it can be turned into bis(trifluoromethyl)benzoic acid or bis(fluoromethyl) benzoate, bis(trifluoromethyl)benzamide and the like by reactions with carbon monoxide in a liquid or gas phase in the presence of a catalyst containing a metal (e.g., palladium) as an activated species.

In the second process, the catalyst is preferably one in which a metal chloride is carried on a carrier. Examples of this carrier are activated carbon, alumina, silica, titania, aluminum fluoride, zirconia, Molecular Sieve, and fluororesins. Of these, activated carbon and titania are preferable, and activated carbon is particularly preferable. The activated carbon is not limited to a particular type. The activated carbon may be prepared from a vegetable raw material such as wood, charcoal, coconut husk coal, palm core coal, or raw ash; a coal such as peat, lignite, brown coal, bituminous coal, or anthracite; a petroleum raw material such as petroleum residue or oil carbon; or a synthetic resin raw material such as carbonated polyvinylidene chloride. The activated carbon may be selected from various commercial activated carbons. Examples of commercial activated carbons that are usable in the second process are activated carbons made of bituminous coal, such as BPL GRANULAR ACTIVATED CARBON (trade name) of TOYO CALGON CO. and 3GX (trade name) of KURARAY CHEMICAL CO., LTD., and coconut husk coals, such as GRANULAR SHIRO SAGI GX, CX and XRC (trade names) of Takeda Chemical Industries, Ltd. and PCB (trade name) of TOYO CALGON CO. An activated carbon used in the second process is generally in the form of granules. Furthermore, it may be in the form of sphere, fiber, powder or honeycomb. Its shape and size are not particularly limited, and may be decided depending on the reactor. As mentioned above, the catalyst preferably contains a metal chloride carried on the carrier. This metal chloride contains at least one metal selected from iron, copper, nickel, cobalt, zinc, titanium, aluminum, tantalum, palladium, potassium and the like. Of these, iron, tantalum and titanium are preferable, and iron is the most preferable. It is also preferable to use iron and at least one other metal together. In this case, the molar ratio of iron to the at least one other metal is preferably within a range of 50/50 to 100/0. The method for preparing the catalyst used in the second process is not particularly limited. It can be prepared by immersing carrier in a solution of at least one metal compound or by spraying such solution on carrier. The metal compound carried on the carrier is in an amount of preferably from 0.01 to 100 parts by weight, more preferably from 1 to 50 parts by weight, per 100 parts by weight of the carrier. If it is less than 0.01 parts by weight, conversion may become too low. If it is greater than 100 parts by weight, the metal compound may not stably be carried on the carrier. The metal compound is preferably one soluble in a solvent (e.g., water, ethanol and acetone), such as chloride or bromide. Specific examples of the metal compound are iron chloride (ferric chloride or ferrous chloride), iron bromide, copper chloride, nickel chloride, cobalt chloride, zinc chloride, titanium chloride, aluminum chloride, tantalum chloride, palladium chloride, and potassium chloride. It is assumed that a metal bromide carried on the carrier turns into a metal chloride in the bromination. Therefore, either metal chloride or metal bromide can be used for the catalyst.

In the second process, the reaction is conducted at a temperature of preferably from 90 to 300° C., more preferably from 100 to 200° C., still more preferably from 110 to 150° C. If it is lower than 90° C., conversion may become too low. If it is higher than 300° C., selectivity of the target product may become too low due to the formation of polybrominated compounds. The reaction pressure does basically not have an influence on the reaction. Thus, it is not particularly limited so long as it is adjusted to being in a range where the raw materials, intermediates and the product do not liquefy. The reaction pressure can be in a range of 0.1–1 MPa. The reaction may be conducted at about normal pressure (atmospheric pressure) or under a little pressurized or reduced condition. The contact time may be in a range of 0.1 to 300 seconds, preferably 5 to 60 seconds.

In the second process, chlorine may be used in an amount of from about 0.7 moles to about 1.5 moles, per mole of bromine. In fact, it suffices to use about 0.8 to about 1.2 moles of chlorine per mole of bromine. Furthermore, it can be adjusted to about 0.9 to about 1.1 moles by suitably controlling the reaction. If the amount of chlorine is less than 0.7 moles, selectivity of the brominated trifluoromethylbenzene becomes high. With this, however, conversion of bromine may become too low. If it is greater than 1.5 moles, it may cause the production of chlorinated trifluoromethylbenzenes and may lower the selectivity of the brominated trifluoromethylbenzene. Furthermore, it makes difficult to treat chlorine during the reaction.

In the second process, it is optional to previously mix bromine with the trifluoromethylbenzene and introduce the resulting mixture into the reactor. Alternatively, they may be separately introduced into the reactor. Similarly, it is optional to previously mix chlorine with bromine and introduce the resulting mixture into the reactor. Alternatively, they may be separately introduced into the reactor. It is also preferable to vaporize such mixture before it is introduced into the reactor.

In the second process, the reactor may be made of a material (e.g., stainless steel, Hastelloy, Monel metal and platinum) so long as it has heat resistance and corrosion resistance against hydrogen fluoride, hydrogen chloride, chlorine, bromine, hydrogen bromide and the like. Furthermore, the reactor may be lined with such material. Although bromine having a tendency to corrode metal is used in the second process, corrosion of the inside of the reactor does almost not occur for a long time.

In the second process, the reaction gas containing the brominated trifluoromethylbenzene, which flows out of the reactor, can be purified by a known method to produce a product. In this purification, bromine, chlorine, bromine chloride and hydrogen chloride contained in the reaction gas can easily be removed by (1) combining a reducing agent (e.g., sodium sulfite) and a basic material (e.g., sodium hydroxide, potassium hydroxide, and calcium hydroxide) for neutralizing the acid components or by (2) flash distillation. The collected bromine in the purification can be used again in the bromination. The crude product obtained by the above purification can be turned into the brominated trifluoromethylbenzene with high purity by distillation.

When it is intended to produce a monobromotrifluoromethylbenzene under atmospheric pressure, the second process may be conducted as follows. At first, a reaction tube is charged with a predetermined amount of a catalyst (i.e., activated carbon carrying thereon iron chloride), followed by heating to a predetermined temperature. After that, predetermined amounts of the trifluoromethylbenzene, bromine and chlorine are introduced into the reaction tube, thereby conducting the reaction. The crude product collected in a receiver is purified by (1) washing with a sodium sulfite aqueous solution and then a sodium hydroxide aqueous solution or by (2) flash distillation, followed by distillation to obtain a brominated trifluoromethylbenzene with high purity. Bromine collected by flash distillation can be used again in the reaction.

The following nonlimitative examples are illustrative of the present invention, and percent (%) therein refers to a real percent unless otherwise stated. Examples 1–4 are illustrative of the first process according to the first aspect of the invention, and the reaction pressures therein are expressed in gauge pressure.

EXAMPLE 1

A 1-liter stainless steel autoclave equipped with a stirrer, a reflux tower and a thermometer protecting tube was charged with 770 g of 1,3-bis(trifluoromethyl)benzene, 288 g of bromine, 15 g of chlorine and 58 g of anhydrous ferric chloride. Then, the autoclave was heated in an oil bath until its internal temperature reaches 110° C. The reaction pressure was maintained within a range of 6–7 kg/cm$^2$ by suitably purging hydrogen chloride generated in the reaction system. The reaction temperature was maintained within a range of 110–115° C. to continue the reaction for 9.5 hr. After the reaction, the autoclave was cooled and allowed to stand still. After that, the content of the autoclave was taken out, and then washed with a sodium sulfite aqueous solution and then with a sodium hydroxide aqueous solution, thereby. collecting 997 g of an organic matter. It was found by a gas chromatographic analysis that this organic matter contains 70.5% of 3,5-bis(trifluoromethyl)bromobenzene, 1.2% of 3,5-bis(trifluoromethyl)-1,2-bromobenzene, and 19.5% of the unreacted 1,3-bis(trifluoromethyl)benzene.

EXAMPLE 2

After taking out the content of the autoclave in Example 1, the autoclave, in which ferric chloride and a small amount of the reaction product remained, was charged again with 770 g of 1,3-bis(trifluoromethyl)benzene, 288, of bromine, and 15 g of chlorine. Then, the autoclave was heated in an oil bath until the internal temperature reaches 110° C. Chlorine was introduced nine (9) times in total into the autoclave with 15 g at each time at intervals of one hour. The reaction pressure was maintained within a range of 6–7 kg/cm$^2$ by suitably purging hydrogen chloride generated in the reaction system. The reaction temperature was maintained within a range of 110–115° C. to continue the reaction for 9.5 hr. After the reaction, the autoclave was cooled and allowed to stand still. After that, the content of the autoclave was taken out, and then washed with a sodium sulfite aqueous solution and then with a sodium hydroxide aqueous solution, thereby collecting 972 g of an organic matter. It was found by a gas chromatographic analysis that this organic matter contains 71.9% of 3,5-bis(trifluoromethyl) bromobenzene, 1.2% of 3,5-bis(trifluoromethyl)1,2-bromobenzene, and 18.2% of the unreacted 1,3-bis (trifluoromethyl)benzene.

EXAMPLE 3

After taking out the content of the autoclave in Example 2, the same procedures of Example 2 were repeated, thereby conducting the reaction again. In fact, the catalyst (ferric chloride) was not replaced with a new one. The content of the autoclave was taken out, and then washed with a sodium sulfite aqueous solution and then with a sodium hydroxide aqueous solution, thereby collecting 978 of an organic matter. It was found by a gas chromatographic analysis that this organic matter contains 69.1% of 3,5-bis (trifluoromethyl)bromobenzene, 1.1% of 3,5-bis (trifluoromethyl)-1,2-bromobenzene, and 20.9% of the unreacted 1,3-bis(trifluoromethyl)benzene.

Corrosion of the autoclave was checked after the reaction, and only a little clouding of the inside of the autoclave was found. This means that the autoclave was almost not corroded by bromine and that the reaction can be conducted repeatedly in this autoclave.

The collected organic matter was purified by distillation, thereby obtaining 663 g of 3,5-bis(trifluoromethly) bromobenzene (purity: 99%). After the content was taken out of the autoclave, the catalyst (ferric chloride) and a small amount of the reaction product, remaining at the bottom of the autoclave, were dissolved in acetone in the autoclave. Then, it was possible to easily take the resulting solution out of the autoclave.

EXAMPLE 4

A 0.5-liter stainless steel autoclave equipped with a stirrer, a reflux tower and a thermometer protecting tube was charged with 146 g of trifluoromethylbenzene, 81 g of bromine, 36 g of chlorine and 32 g of anhydrous ferric chloride. Then, the autoclave was heated in an oil bath until the internal temperature reaches 110° C. The reaction was continued for 7.0 hr, while the reaction pressure was maintained within a range of 17–19.5 kg/cm$^2$ and the reaction temperature was maintained at 110° C. After the reaction, the autoclave was cooled and allowed to stand still. After that, the content of the autoclave was taken out, and then washed with a sodium sulfite aqueous solution and then with a sodium hydroxide aqueous solution, thereby collecting 197 g of an organic matter. It was found by a gas chromatographic analysis that this organic matter contains 62.0% of 3-bromotrifluoromethylbenzene and the unreacted trifluoromethylbenzene.

The following Catalyst Preparation Examples 1–12 and Examples 5–8 are illustrative of the second aspect of the invention.

CATALYST PREPARATION EXAMPLE 1

A 1-liter ferric chloride solution was prepared by dissolving 300 g of anhydrous ferric chloride (FeCl$_3$) in a 1.2N hydrochloric acid aqueous solution. Then, 2-liter of a coal-origin, columnar, granular, activated carbon (4–8 meshes), 3GX (trade name) of KURARAY CHEMICAL CO., LTD., were immersed in the ferric chloride solution, followed by allowing it to stand still for one day and one night. Then, the activated carbon was separated from the solution by filtration, followed by drying in an eggplant-type flask at a temperature of 120–130° C. under vacuum using an evaporator, thereby obtaining an activated carbon carrying thereon ferric chloride. Then, a cylindrical reaction tube, made of stainless steel (SUS316) and equipped with an electric furnace and having a diameter of 3.75 cm and an axial length of 160 cm, was charged with 1.5 liter of the obtained activated carbon. Then, the reaction tube was heated to 300° C., while nitrogen was allowed to flow therethrough. After confirming that steam flow therefrom stopped, the reaction tube was maintained under the same condition for 1 hr, thereby preparing a first catalyst (activated carbon carrying thereon ferric chloride, FeCl$_3$/C).

CATALYST PREPARATION EXAMPLE 2

A 100 ml ferrous chloride solution was prepared by dissolving 30 g of anhydrous ferrous chloride (FeCl$_2$) in a 1.2N hydrochloric acid aqueous solution. Then, 100 ml of a coconut-husk-origin, columnar, granular activated carbon (4/6-1 mesh), GRANULAR SHIRO SAGI G2X (trade name) of Takeda Chemical Industries, Ltd., were immersed in the ferrous chloride solution, followed by allowing it to stand still for one day and one night. Then, the activated carbon was separated from the solution by filtration, followed by drying in an eggplant-type flask at a temperature of 120–130° C. under vacuum using an evaporator, thereby obtaining a second catalyst (activated carbon carrying thereon ferrous iron, $FeCl_2/C$).

CATALYST PREPARATION EXAMPLE 3

A 100 ml titanium tetrachloride solution was prepared by dissolving 20 g of titanium tetrachloride ($TiCl_4$) in a 1.2N hydrochloric acid aqueous solution. Then, 100 ml of a columnar, granular, activated carbon (4/6-1 mesh), GRANULAR SHIRO SAGI (trade name) of Takeda Chemical Industries, Ltd., were immersed in the titanium tetrachloride solution, followed by allowing it to stand still for one day and one night. Then, the activated carbon was separated from the solution by filtration, followed by drying in an eggplant-type flask at a temperature of 120–130° C. under vacuum using an evaporator, thereby obtaining a third catalyst (activated carbon carrying thereon titanium tetrachloride, $TiCl_4/C$).

CATALYST PREPARATION EXAMPLE 4

A 100 ml tantalum pentachloride solution was prepared by dissolving 15 g of tantalum pentachloride ($TaCl_5$) in a 1.2N hydrochloric acid aqueous solution. Then, 100 ml of a columnar, granular, activated carbon (4/6-1 mesh), GRANULAR SHIRO SAGI (trade name) of Takecla Chemical Industries, Ltd., were immersed in the tantalum pentachloride solution, followed by allowing it to stand still for one day and one night. Then, the activated carbon was separated from the solution by filtration, followed by drying in an eggplant-type flask at a temperature of 120–130° C. under vacuum using an evaporator, thereby obtaining a fourth catalyst (activated carbon carrying thereon tantalum pentachloride, $TaCl_5/C$).

CATALYST PREPARATION EXAMPLE 5

A 100 ml ferric chloride solution was prepared by dissolving 30 g of anhydrous ferric chloride in a 1.2N hydrochloric acid aqueous solution. Then, 100 ml of titania were immersed in the ferric chloride solution, followed by allowing it to stand still for one day and one night. Then, the titania was separated from the solution by filtration, followed by drying in an eggplant-type flask at a temperature of 120–130° C. under vacuum using an evaporator, thereby obtaining a fifth catalyst (titania carrying thereon ferric chloride, $FeCl_3/TiO_2$).

CATALYST PREPARATION EXAMPLE 6

A 100 ml solution was prepared by dissolving 30 g of anhydrous ferric chloride and 3 g of potassium chloride (KCl) in a 1.2N hydrochloric acid aqueous solution. Then, 100 ml of a columnar, granular, activated carbon (4–8 meshes) of KURARAY CHEMICAL CO., LTD. were immersed in the solution, followed by allowing it to stand still for one day and one night. Then, the activated carbon was separated from the solution by filtration, followed by drying in an eggplant-type flask at a temperature of 120–130° C. under vacuum using an evaporator, thereby obtaining a sixth catalyst (activated carbon carrying thereon ferric chloride and potassium chloride, $KCl/FeCl_3/C$).

CATALYST PREPARATION EXAMPLE 7

A seventh catalyst (activated carbon carrying thereon ferric chloride and cupric chloride, $CuCl_2/FeCl_3/C$) was prepared by the same process as that of Catalyst Preparation Example 6, except that 3 g of potassium chloride were replaced with 10 g of cupric chloride (CuCl2).

CATALYST PREPARATION EXAMPLE 8

An eighth catalyst (activated carbon carrying thereon ferric chloride and zinc chloride, $ZnCl_2/FeCl_3/C$) was prepared by the same process as that of Catalyst Preparation Example 6, except that 3 g of potassium chloride were replaced with 10 g of zinc chloride ($ZnCl_2$).

CATALYST PREPARATION EXAMPLE 9

A ninth catalyst (activated carbon carrying thereon ferric chloride and aluminum chloride, $AlCl_3/FeCl_3/C$) was prepared by the same process as that of Catalyst Preparation Example 6, except that 3 g of potassium chloride were replaced with 10 g of anhydrous aluminum chloride ($AlCl_3$).

CATALYST PREPARATION EXAMPLE 10

A tenth catalyst (activated carbon carrying thereon ferric chloride and nickel chloride, $NiCl_2/FeCl_3/C$) was prepared by the same process as that of Catalyst Preparation Example 6, except that a combination of 30 g of anhydrous ferric chloride and 3 g of potassium chloride was replaced with a combination of 50 g of ferric chloride hexahydrate ($FeCl_3.6H_2O$) and 18 g of nickel chloride hexahydrate ($NiCl_2.6H_2O$).

CATALYST PREPARATION EXAMPLE 11

An eleventh catalyst (activated carbon carrying thereon ferric chloride and cobalt chloride, $CoCl_2/FeCl_3/C$) was prepared by the same process as that of Catalyst Preparation Example 10, except that 18 g of nickel chloride hexahydrate were replaced with 18 g of cobalt chloride hexahydrate ($CoCl_2.6H_2O$).

CATALYST PREPARATION EXAMPLE 12

A twelfth catalyst (activated carbon carrying thereon ferric chloride and palladium chloride, $PdCl_2/FeCl_3/C$) was prepared by the same process as that of Catalyst Preparation Example 10, except that 18 g of nickel chloride hexahydrate were replaced with 2 g of palladium chloride ($PdCl_2$).

EXAMPLE 5

In this example, a reaction apparatus having a reaction tube and a receiver was used. This reaction tube made of stainless steel (SUS 316) had a diameter of 3.75 cm and an axial length of 160 cm and was equipped with (1) a vaporizer on its inlet side and (2) a heat medium device for heating the reaction tube. Furthermore, the reaction apparatus was provided with a reflux condenser on the outlet side of the receiver. At first, the reaction tube was charged with 1.5-liter of the first catalyst of Catalyst Preparation Example 1. Then, the reaction tube was heated by setting the heat medium temperature at 130° C. When the temperature of the first catalyst reached 130° C., it was started to continuously introduce 1,3-bis(trifluoromethyl)benzene, bromine and chlorine through the vaporizer at their respective rates of 554 g (2.6 moles) per hour, 208 g (1.3 moles) per hour and 92 g (1.3 moles) per hour. The reaction gas flowing out of the reaction tube was condensed in the receiver, thereby removing hydrogen chloride that was not condensed. The reaction was continued for 1,000 hr by supplying 554 kg of 1,3-bis(trifluoromethyl)benzene, 208 kg of bromine and 92 kg of chlorine, thereby collecting 745 kg of a crude product in the receiver. Then, this crude product was washed with a sodium sulfite aqueous solution and then a sodium hydroxide aqueous solution, thereby removing bromine, chlorine and the like. A product obtained by this washing was found by a gas chromatographic analysis to contain 69.3% of 3,5-bis(trifluoromethyl)bromobenzene, 19.4% of 1,3-bis (trifluoromethyl)benzene, 0.3% of 2,4-bis(trifluoromethyl) bromobenzene, 3.4% of 3,5-bis(trifluoromethyl) chlorobenzene, 3.4% of 3,5-bis(trifluoromethyl) bromobenzene, and 4.2% of others. This product was purified by distillation, thereby obtaining 476 kg of 3,5-bis (trifluoromethyl)bromobenzene having a purity of 97%. The corrosion of the reaction tube after 1,000 hr reaction was almost not found.

EXAMPLE 6

In this example, a reaction apparatus was used which was the same as that of Example 5, except that the reaction tube had a diameter of 4 cm and an axial length of 40 cm. At first, the reaction tube was charged with 100 ml of the first catalyst of Catalyst Preparation Example 1. Then, the reaction tube was heated by setting the heat medium temperature at 130° C. When the temperature of the first catalyst reached 130° C., it was started to continuously introduce trifluoromethylbenzene, bromine and chlorine through the vaporizer at their respective rates of 51 g per hour, 28 g per hour and 10 g per hour. The reaction gas flowing out of the reaction tube was condensed in the receiver, thereby removing hydrogen chloride that was not condensed. The reaction was continued for 6 hr by supplying 306 g of trifluoromethylbenzene, 169 g of bromine and 61 kg of chlorine, thereby collecting 320 g of a crude product in the receiver. Then, this crude product was washed with a sodium sulfite aqueous solution and then a sodium hydroxide aqueous solution, thereby removing bromine, chlorine and the like. A product obtained by this washing was found by a gas chromatographic analysis to contain 42.0% of 3-bromo (trifluoromethyl)benzene, 29.5% of trifluoromethylbenzene, 3.1% of 4-bromo(trifluoromethyl)benzene, 0.4% of 2-bromo (trifluoromethyl)benzene, 13.0% of dibromo (trifluoromethyl)benzene, 1.2% of 3-chloro(trifluoromethyl) benzene, and 10.8% of others.

EXAMPLE 7

In this example, the reaction was conducted in the same manner as that of Example 6 except that it was started to continuously introduce 1,4-bis(trifluoromethyl)benzene, bromine and chlorine through the vaporizer at their respective rates of 38 g per hour, 14.4 g per hour and 5.4 g per hour and that the reaction was continued for 6 hr by supplying 230 g of 1,4-bis(trifluoromethyl)benzene, 86 g of bromine and 32 g of chlorine, thereby collecting 270 g of a crude product in the receiver. Then, this crude product was washed with a sodium sulfite aqueous solution and then a sodium hydroxide aqueous solution, thereby removing bromine, chlorine and the like. A product obtained by this washing was found by a gas chromatographic analysis to contain 12.0% of 2,5-bis(trifluoromethyl)bromobenzene, 62.0% of 1,4-bis(trifluoromethylbenzene, 4.8% of 2,5-bis (trifluoromethyl)chlorobenzene, 13.8% of 2,5-bis (trifluoromethyl)dibromobenzene, and 7.4% of others.

EXAMPLE 8

In this example, the reaction was conducted eleven (11) times in the same manner as that of Example 6 except that the first catalyst was replaced with each of the second to twelfth catalysts of Catalyst Preparation Examples 2–12, that it was started to continuously introduce 1,3-bis (trifluoromethyl)benzene, bromine and chlorine through the vaporizer at their respective rates of 38 g (0.18 moles) per hour, 14.4 g (0.089 moles) per hour and 5.4 g (0.076 moles) per hour, and that the reaction was continued for 6 hr by supplying 230 g of 1,3-bis(trifluoromethyl)benzene, 86 g of bromine and 32 g of chlorine, thereby collecting a crude product in the receiver. Then, this crude product was washed with a sodium sulfite aqueous solution and then a sodium hydroxide aqueous solution, thereby removing bromine, chlorine and the like. A product obtained by this washing was found by a gas chromographic analysis to have a chemical composition shown in Table. For example, the molar ratio of potassium to iron in the sixth catlyst of Catalyst Preparation Example 6 was 0.22/1, as shown in Table, and the other metal/metal molar ratios shown in Table were similarly determined.

TABLE

| Catalyst Preparation Examples | Catalyst Composition Metal Compound/Carrier (Metal/Metal Molar Ratio) | Product Composition (areal %) | | | | | |
|---|---|---|---|---|---|---|---|
| | | A* | B* | C* | D* | E* | F* |
| 2 | FeCl$_2$/C | 26.5 | 59.4 | 0.2 | 3.7 | 3.7 | 6.5 |
| 3 | TiCl$_4$/C | 84.3 | 5.6 | 0.4 | 0.1 | 1.1 | 8.1 |
| 4 | TaCl$_5$/C | 81.8 | 10.9 | 0.3 | — | 2.8 | 4.2 |
| 5 | FeCl$_3$/TiO$_2$ | 52.2 | 26.6 | 0.8 | 3.0 | 5.3 | 12.1 |
| 6 | KCl/FeCl$_3$/C (0.22/1) | 21.5 | 65.6 | 0.2 | 2.5 | 4.2 | 6.0 |
| 7 | CuCl$_2$/FeCl$_3$/C (0.12/1) | 14.3 | 70.5 | 0.2 | 4.8 | 3.8 | 6.4 |
| 8 | ZnCl$_2$/FeCl$_3$/C (0.40/1) | 25.6 | 62.4 | 0.3 | 2.1 | 4.2 | 5.4 |
| 9 | AlCl$_3$/FeCl$_3$/C (0.40/1) | 26.6 | 63.6 | 0.2 | 2.4 | 4.6 | 3.7 |
| 10 | NiCl$_2$/FeCl$_3$/C (0.40/1) | 17.2 | 66.9 | 0.2 | 3.9 | 4.6 | 7.2 |
| 11 | CoCl$_2$/FeCl$_3$/C (0.40/1) | 14.6 | 69.5 | 0.2 | 4.9 | 3.9 | 6.9 |
| 12 | PdCl$_2$/FeCl$_3$/C (0.06/1) | 13.8 | 70.8 | 0.2 | 4.5 | 4.5 | 6.2 |

*A: 1,3-bis(trifluoromethyl)benzene
*B: 3,5-bis(trifluoromethyl)bromobenzene
*C: 2,4-bis(trifluoromethyl)bromobenzene
*D: dibromo compound
*E: 3,5-bis(trifluoromethyl)chlorobenzene
*F: others

What is claimed is:

1. A process for producing a brominated trifluoromethylbenzene represented by the general formula (1), said process comprising brominating in a liquid phase a trifluoromethylbenzene, represented by the general formula (2), by bromine in the presence of an iron-containing catalyst under a condition that said bromine is coexistent with chlorine,

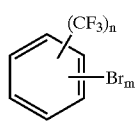
(1)

where n is an integer of 1–2, and m is an integer of 1–3

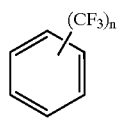
(2)

where n is an integer of 1–2.

2. A process for producing 3,5-bis(trifluoromethyl)bromobenzene, said process comprising brominating in a liquid phase 1,3-bis(trifluoromethyl)benzene by bromine in the presence of iron chloride under a condition that said bromine is coexistent with chlorine, at a temperature of 50–200° C., with a molar ratio of said bromine to said 1,3-bis(trifluoromethyl)benzene of 0.5–2, and with a molar ratio of said chlorine to said bromine of 1–2.

3. A process according to claim 1, wherein a molar number of each of said bromine and said chlorine is 0.5 m moles or more for each m number.

4. A process according to claim 1, wherein a molar ratio of said bromine to said 1,3-bis(trifluoromethyl)benzene to obtain 3,5-bis(trifluoromethyl)bromobenzene is from 0.5 to 2.

5. A process according to claim 1, wherein a molar ratio of said chlorine to said bromine is from 1 to 2.

6. A process according to claim 1, wherein said bromine in a reaction system of said brominating is in excess of said chlorine.

7. A process according to claim 1, wherein said iron-containing catalyst comprises an iron halide.

8. A process according to claim 1, wherein iron contained in said catalyst is in an amount of 0.1–100 moles relative to 100 moles of said trifluoromethylbenzene.

9. A process according to claim 1, wherein said brominating is conducted at a temperature of 50 to 200° C.

10. A process according to claim 9, wherein said temperature is from 50 to 150° C.

11. A process according to claim 1, wherein said brominating is conducted under a pressure of from 1 to 100 kg/cm².

12. A process for producing a brominated trifluoromethylbenzene represented by the general formula (1), said process comprising brominating in a gas phase a trifluoromethylbenzene, represented by the general formula (2), by bromine in the presence of a catalyst under a condition that said bromine is coexistent with chlorine,

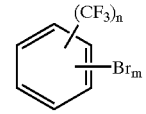
(1)

where n is an integer of 1–2, and m is an integer of 1–3

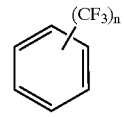
(2)

where n is an integer of 1–2, and where said catalyst comprises a compound of at least one metal selected from the group consisting of iron., tantalum and titanium.

13. A process according to claim 12, wherein said catalyst comprises a metal chloride carried on a carrier.

14. A process according to claim 12, wherein said catalyst comprises an activated carbon carrying thereon iron chloride.

15. A process for producing 3,5-bis(trifluoromethyl)bromobenzene, said process comprising brominating in a gas phase 1,3-bis(trifluoromethyl)benzene by bromine in the presence of an activated carbon carrying thereon iron chloride, under a condition that said bromine is coexistent with chlorine, at a temperature of 90–200° C., with a molar ratio of said bromine to said 1,3-bis(trifluoromethyl)benzene of 0.5–2, with a molar ratio of said chlorine to said bromine of 0.7–1.5, and with a contact time of 0.1 to 300 seconds.

16. A process according to claim 12, wherein said at least one metal comprises iron.

17. A process according to claim 12, wherein said brominating is conducted at a temperature of 90–300° C.

18. A process according to claim 12, wherein said brominating is conducted with a contact time of 0.1–300 seconds.

19. A process according to claim 12, wherein a molar number of said bromine is 0.5 m moles or more for each m number.

20. A process according to claim 12, wherein a molar ratio of said bromine to said 1,3-bis(trifluoromethyl)benzene to obtain 3,5-bis(trifluoromethyl)bromobenzene is from 0.5 to 2.

21. A process according to claim 12, wherein a molar ratio of said chlorine to said bromine is from 0.7–1.5.

* * * * *